(12) United States Patent
Boutier et al.

(10) Patent No.: US 11,952,322 B2
(45) Date of Patent: Apr. 9, 2024

(54) STABILIZATION OF 1-CHLORO-3,3,3-TRIFLUOROPROPENE

(71) Applicant: Arkema France, Colombes (FR)

(72) Inventors: Jean-Christophe Boutier, Pierre-Benite (FR); Wissam Rached, Colombes (FR)

(73) Assignee: ARKEMA FRANCE, Colombes (FR)

( * ) Notice: Subject to any disclaimer, the term of this patent is extended or adjusted under 35 U.S.C. 154(b) by 369 days.

(21) Appl. No.: 17/280,547

(22) PCT Filed: Sep. 9, 2019

(86) PCT No.: PCT/FR2019/052074
§ 371 (c)(1),
(2) Date: Mar. 26, 2021

(87) PCT Pub. No.: WO2020/065166
PCT Pub. Date: Apr. 2, 2020

(65) Prior Publication Data
US 2021/0340083 A1    Nov. 4, 2021

(30) Foreign Application Priority Data
Sep. 26, 2018  (FR) ..................... 1858817

(51) Int. Cl.
C07C 17/42   (2006.01)
B01J 20/18   (2006.01)
B01J 20/28   (2006.01)
F02C 1/00    (2006.01)

(52) U.S. Cl.
CPC .............. *C07C 17/42* (2013.01); *B01J 20/18* (2013.01); *B01J 20/28052* (2013.01); *F02C 1/00* (2013.01); *F05D 2220/76* (2013.01)

(58) Field of Classification Search
CPC .......... C07C 17/42; C07C 21/18; B01J 20/18; B01J 20/28052
See application file for complete search history.

(56) References Cited

U.S. PATENT DOCUMENTS

| | | |
|---|---|---|
| 2,583,812 A | 1/1952 | Briggs et al. |
| 2,882,243 A | 4/1959 | Milton |
| 4,013,566 A | 3/1977 | Taylor |
| 5,616,819 A | 4/1997 | Boyce et al. |
| 5,684,219 A | 11/1997 | Boyce |
| 5,705,779 A | 1/1998 | Demmin et al. |
| 5,877,359 A | 3/1999 | Elsheikh |
| 6,166,274 A | 12/2000 | Chen et al. |
| 6,403,847 B1 | 6/2002 | Nakada et al. |
| 8,404,907 B2 | 3/2013 | Nair et al. |
| 8,426,656 B2 | 4/2013 | Merkel et al. |
| 8,436,217 B2 | 5/2013 | Wang et al. |
| 8,704,017 B2 | 4/2014 | Pokrovski et al. |
| 8,877,990 B2 | 11/2014 | Fukuju et al. |
| 9,255,045 B2 | 2/2016 | Pigamo et al. |
| 9,643,903 B2 | 5/2017 | Pokrovski et al. |
| 9,834,499 B2 | 12/2017 | Pigamo et al. |
| 10,077,221 B2 | 9/2018 | Bonnet et al. |
| 10,227,275 B2 | 3/2019 | Pigamo et al. |
| 10,343,963 B2 | 7/2019 | Bonnet |
| 10,427,998 B2 | 10/2019 | Pigamo et al. |
| 10,532,965 B2 | 1/2020 | Pigamo et al. |
| 10,669,465 B2 | 6/2020 | Rached |
| 10,858,561 B2 | 12/2020 | Abbas et al. |
| 11,028,027 B2 | 6/2021 | Wendlinger et al. |
| 11,034,635 B2 | 6/2021 | Wendlinger et al. |
| 11,084,768 B2 | 8/2021 | Wendlinger et al. |
| 11,242,304 B2 | 2/2022 | Pigamo et al. |
| 2001/0014707 A1 | 8/2001 | Thomas et al. |
| 2010/0191025 A1 | 7/2010 | Perdrieux |
| 2011/0196178 A1 | 8/2011 | Nyberg |
| 2011/0197602 A1 | 8/2011 | Abbas et al. |
| 2011/0201853 A1 | 8/2011 | Tung et al. |
| 2011/0218370 A1 | 9/2011 | Elsheikh et al. |
| 2011/0245549 A1 | 10/2011 | Merkel et al. |
| 2011/0259828 A1 | 10/2011 | Bouvier et al. |
| 2012/0059199 A1 | 3/2012 | Pokrovski et al. |
| 2012/0172636 A1 | 7/2012 | Pokrovski |
| 2012/0190902 A1 | 7/2012 | Nyberg |
| 2012/0226081 A1 | 9/2012 | Elsheikh et al. |

(Continued)

FOREIGN PATENT DOCUMENTS

| | | |
|---|---|---|
| CN | 101687735 A | 3/2010 |
| CN | 102216247 A | 10/2011 |

(Continued)

OTHER PUBLICATIONS

International Search Report (PCT/ISA/210) with translation and Written Opinion (PCT/ISA/237) dated Jan. 22, 2020, by the European Patent Office as the International Searching Authority for International Application No. PCT/FR2019/052074.
Test No. 102: Melting point/Melting range, OECD guidelines for the testing of chemical products, Section 1, OECD Editions, Paris, 1995, available at http://dx.doi.org/10.1787/9789264069534-fr (with English translation) (17 pages).
Breck, Donald W., et al., "Zeolite Molecular Sieves", John Wiley & Sons Eds, (1974), 159 pages.
U.S. Appl. No. 17/557,668, **Pigamo et al.
**Pigamo, Anne, et al., U.S. Appl. No. 17/557,668 entitled "Method for Producing 1-Chloro-3,3,3-Trifluoropropene," filed Dec. 21, 2021.

(Continued)

*Primary Examiner* — Jafar F Parsa
(74) *Attorney, Agent, or Firm* — BUCHANAN, INGERSOLL & ROONEY PC

(57) ABSTRACT

The joint use of a C3 to C6 alkene compound comprising a sole double bond and of at least one molecular sieve for limiting or preventing the isomerization of trans-1-chloro-3,3,3-trifluoropropene to cis-1-chloro-3,3,3-trifluoropropene, and/or for limiting or preventing the degradation of trans-1-chloro-3,3,3-trifluoropropene. Also, a method for heating or cooling a fluid or a body, to a method for producing electricity and to a heat transfer installation.

10 Claims, No Drawings

(56) References Cited

U.S. PATENT DOCUMENTS

| | | |
|---|---|---|
| 2012/0256119 A1 | 10/2012 | Bouvier et al. |
| 2012/0256120 A1 | 10/2012 | Bouvier et al. |
| 2012/0271070 A1 | 10/2012 | Wang et al. |
| 2012/0329893 A1 | 12/2012 | Abbas |
| 2013/0037058 A1 | 2/2013 | Abbas |
| 2013/0211154 A1 | 8/2013 | Cottrell et al. |
| 2013/0261353 A1 | 10/2013 | Pokrovski et al. |
| 2013/0261354 A1 | 10/2013 | Merkel |
| 2014/0077122 A1 | 3/2014 | Fukushima |
| 2014/0213831 A1 | 7/2014 | Nyberg |
| 2014/0221704 A1 | 8/2014 | Tung et al. |
| 2014/0264173 A1 | 9/2014 | Merkel et al. |
| 2015/0152235 A1 | 6/2015 | Abbas |
| 2015/0197467 A1 | 7/2015 | Pigamo et al. |
| 2016/0023974 A1 | 1/2016 | Bonnet et al. |
| 2016/0115104 A1 | 4/2016 | Pigamo et al. |
| 2016/0272561 A1 | 9/2016 | Rached et al. |
| 2017/0050904 A1 | 2/2017 | Ondrus |
| 2017/0081263 A1 | 3/2017 | Klausmeyer et al. |
| 2017/0174965 A1 | 6/2017 | Tsuchiya et al. |
| 2017/0210686 A1 | 7/2017 | Pigamo et al. |
| 2018/0015407 A1 | 1/2018 | Vittenet et al. |
| 2018/0093934 A1 | 4/2018 | Pigamo et al. |
| 2018/0148394 A1 | 5/2018 | Pigamo et al. |
| 2018/0164007 A1 | 6/2018 | Tsuboe et al. |
| 2018/0346396 A1 | 12/2018 | Pigamo et al. |
| 2018/0354875 A1 | 12/2018 | Bonnet |
| 2019/0048241 A1 | 2/2019 | Abbas et al. |
| 2019/0152883 A1 | 5/2019 | Pigamo et al. |
| 2019/0276721 A1 | 9/2019 | Rached |
| 2019/0375698 A1 | 12/2019 | Pigamo et al. |
| 2020/0407293 A1 | 12/2020 | Wendlinger et al. |
| 2021/0002188 A1 | 1/2021 | Wendlinger et al. |
| 2021/0002189 A1 | 1/2021 | Wendlinger et al. |
| 2021/0238112 A1 | 8/2021 | Pigamo et al. |
| 2021/0261485 A1 | 8/2021 | Hisler et al. |

FOREIGN PATENT DOCUMENTS

| | | |
|---|---|---|
| EP | 0 940 382 A1 | 9/1999 |
| EP | 1566600 A1 | 8/2005 |
| EP | 2035117 A1 | 3/2009 |
| FR | 1 257 034 | 1/1960 |
| FR | 2768727 A1 | 3/1999 |
| FR | 2973717 A1 | 10/2012 |
| FR | 2973809 A1 | 10/2012 |
| FR | 3032131 A1 | 8/2016 |
| FR | 3041632 A1 | 3/2017 |
| JP | 2000-95714 A | 4/2000 |
| JP | 2012-509324 A | 4/2012 |
| WO | WO 01/81353 A1 | 11/2001 |
| WO | 2007144632 A1 | 12/2007 |
| WO | WO 2008/127940 A1 | 10/2008 |
| WO | WO 2008/149011 A2 | 12/2008 |
| WO | WO 2008/149011 A3 | 12/2008 |
| WO | WO 2010/059496 A1 | 5/2010 |
| WO | 2010063975 A1 | 6/2010 |
| WO | WO 2010/111067 A1 | 9/2010 |
| WO | 2012067980 A2 | 5/2012 |
| WO | 2012/157763 A1 | 11/2012 |
| WO | 2014/080868 A1 | 5/2014 |
| WO | WO 2014/116562 A1 | 7/2014 |
| WO | WO 2015/175791 A1 | 11/2015 |
| WO | 2016146940 A1 | 9/2016 |
| WO | 2016/189717 A1 | 12/2016 |
| WO | 2017031046 A1 | 2/2017 |

OTHER PUBLICATIONS

Office Action (Notice of Reasons for Refusal) dated Jun. 6, 2023, by the Japanese Patent Office in corresponding Japanese Patent Application No. 2021-516872, and an English Translation of the Office Action. (6 pages).

Ghanem, Akram, et al., "Static mixers; Mechanisms, applications, and characterization methods—A review," Chemical Engineering Research and Design, 2014, pp. 205-228, vol. 92, Elsevier B.V., NL.

STABILIZATION OF 1-CHLORO-3,3,3-TRIFLUOROPROPENE

FIELD OF THE INVENTION

The present invention relates to compounds for stabilizing 1-chloro-3,3,3-trifluoropropene and more precisely for limiting or preventing the isomerization of the trans form into the cis form, or the degradation of the compound. The invention also relates to the use of such compounds in heat transfer applications.

TECHNICAL BACKGROUND trans-1-Chloro-3,3,3-trifluoropropene (HCFO-1233zdE) is a product with a low global warming potential (GWP). Its thermodynamic and thermophysical properties are very suitable for its use as a heat transfer fluid in cooling, air conditioning, electricity production (notably using Organic Rankine cycles) and high temperature heat pump applications.

HCFO-1233zdE shows instability which is mainly exhibited at a relatively high temperature. This instability consists of isomerization of a fraction of the initial feedstock, leading to the formation of cis-1-chloro-3,3,3-trifluoropropene (HCFO-1233zdZ).

However, HCFO-1233zdZ is a product which is less volatile than HCFO-1233zdE. The boiling point is about 40° C. for the Z isomer, and about 18.3° C. for the E isomer. This difference entails a change in the thermodynamic and thermophysical properties of the product in facilities, and loss of performance when isomerization takes place.

WO 2016/146940 describes the use of C3-C6 alkene compounds for stabilizing 1-chloro-3,3,3-trifluoropropene.

FR 3 041 632 describes a process for purifying and drying a hydrofluoroolefin stream comprising a hydrofluoroolefin chosen from HFO-1234yf and HCFO-1233zd, water and impurities based on halocarbon compounds, characterized in that said stream is placed in contact with an adsorbent.

FR 2 973 809 relates to the use of zeolites for improving the thermal stability of any type of oil, and in particular of oils or oil-based formulations included in the composition of refrigerant fluids.

FR 2 973 717 relates to a process for reducing the acidity of refrigerant fluids, notably of refrigerant fluids used in refrigeration and air-conditioning devices, the process comprising a step of placing the refrigerant fluid in contact with at least one zeolitic adsorbent.

FR 3 032 131 describes the use, for the separation and/or drying of gases (notably hydrofluorocarbons or hydrofluoroolefins), of specific zeolitic adsorbent materials.

FR 3 041 632 relates to a process for purifying and drying a hydrofluoroolefin stream comprising a hydrofluoroolefin, water and impurities based on halocarbon compounds, characterized in that said stream is placed in contact with an adsorbent (notably a molecular sieve).

WO 2012/067980 relates to a process for manufacturing HFO-1234yf via the dehydrohalogenation of a 2-chloro-1,1,1,2-tetrafluoropropane stream which does not contain any impurities such as halogenated propanes, propenes and propynes.

WO 2017/031046 describes a method for removing acidic impurities present in haloolefins such as HFO-1234ze, HFO-1234yf, HCFO-1233zd and HCFO-1233xf, the method comprising passing the olefin stream through a solid adsorbent which may notably be a molecular sieve.

EP 2 035 117 relates to a process for drying a fluid comprising fluoropropene, the process comprising a step of placing the fluid in contact with a dehydrating agent comprising a molecular sieve.

There is a need for an improved method for limiting or preventing the isomerization of HCFO-1233zdE to HCFO-1233zdZ, notably in vapor compression systems such as air conditioning, refrigeration, heat pump and organic Rankine cycle systems, and most particularly systems including a flooded evaporator.

SUMMARY OF THE INVENTION

Firstly, the invention relates to the combined use of a C3 to C6 alkene compound including only one double bond and of at least one molecular sieve for limiting or preventing the isomerization of trans-1-chloro-3,3,3-trifluoropropene to cis-1-chloro-3,3,3-trifluoropropene, and/or for limiting or preventing the degradation of trans-1-chloro-3,3,3-trifluoropropene.

In certain embodiments, the alkene compound is a butene or a pentene.

In certain embodiments, the alkene compound has:
  a boiling point of less than or equal to 100° C., preferably less than or equal to 75° C. and more particularly preferably less than or equal to 50° C.; and/or
  a solidification temperature of less than or equal to 0° C., preferably less than or equal to −25° C. and more particularly preferably less than or equal to −50° C.

In certain embodiments, the alkene compound is 2-methylbut-2-ene.

In certain embodiments, the at least one molecular sieve is at least one zeolitic adsorbent.

In certain embodiments, the at least one zeolitic adsorbent is chosen from A-type zeolites, faujasite type zeolites, Y-type zeolites and mixtures thereof.

In certain embodiments, the at least one zeolitic adsorbent is chosen from zeolite 3A, zeolite 5A, zeolite 13X and mixtures thereof.

In certain embodiments, at least one molecular sieve for adsorbing air and at least one molecular sieve for adsorbing water are used, preferably arranged in successive layers in a cartridge.

The invention also relates to a process for heating or cooling a fluid or a body by means of a vapor compression circuit containing a heat transfer fluid, said process comprising in succession: evaporation of the heat transfer fluid, compression of the heat transfer fluid, condensation of the heat transfer fluid and expansion of the heat transfer fluid, in which the heat transfer fluid comprises trans-1-chloro-3,3,3-trifluoropropene and a C3 to C6 alkene compound, and in which the heat transfer fluid is placed in contact with a molecular sieve.

The invention also relates to a process for producing electricity by means of a heat engine containing a heat transfer fluid, said process comprising in succession: evaporation of the heat transfer fluid, expansion of the heat transfer fluid in an electricity-generating turbine, condensation of the heat transfer fluid and compression of the heat transfer fluid, in which the heat transfer fluid comprises trans-1-chloro-3,3,3-trifluoropropene and a C3 to C6 alkene compound, and in which the heat transfer fluid is placed in contact with a molecular sieve.

In certain embodiments, the heat transfer fluid reaches a temperature of greater than or equal to 100° C., preferably greater than or equal to 150° C., more preferably greater than or equal to 200° C., more preferably greater than or equal to 220° C.

The invention also relates to a heat transfer facility comprising a vapor compression circuit containing a heat transfer fluid, the heat transfer fluid comprising trans-1-chloro-3,3,3-trifluoropropene and a C3 to C6 alkene compound, the vapor compression circuit being equipped with a molecular sieve.

In certain embodiments, the facility is chosen from mobile or stationary facilities for heat-pump heating, air conditioning, refrigeration or freezing and heat engines.

In certain embodiments, the alkene compound is 2-methylbut-2-ene.

In certain embodiments, the molecular sieve is a zeolitic adsorbent or, preferably, at least two zeolitic adsorbents arranged in layers.

The present invention meets the abovementioned need. It more particularly provides an improved means for stabilizing HCFO-1233zdE, notably in vapor compression systems such as air conditioning, refrigeration, heat pump and heat engine systems, most particularly systems including a flooded evaporator, and most particularly in high temperature applications.

Specifically, the present inventors have observed that the HCFO-1233zeE isomerization and degradation problems that occur at high temperature are promoted by the presence of air and humidity, or even acidity, so that these problems occur to a certain extent despite the presence of a stabilizer. The use of a molecular sieve makes it possible to limit or prevent the presence of air and humidity in the refrigeration circuit and, surprisingly, does not affect C3 to C6 alkene stabilizers.

DESCRIPTION OF EMBODIMENTS OF THE INVENTION

The invention is now described in greater detail and in a nonlimiting manner in the description that follows.

Unless otherwise mentioned, the indicated compound proportions are given as mass percentages throughout the patent application.

The invention proposes placing HCFO-1233zdE in contact with a C3 to C6 alkene compound including only one double bond, and also with at least one molecular sieve in order to stabilize HCFO-1233zdE, i.e. to limit or prevent its isomerization to HCFO-1233zdZ, notably at high temperatures and notably when traces of humidity and/or air and/or acidity are present. This placing in contact also makes it possible to stabilize HCFO-1233zdE while avoiding its degradation. The term "degradation" means the conversion of HCFO-1233zd molecules into other species. The degradation of HCFO-1233zdE may notably be reflected by an increase in the concentration of fluoride and chloride ions present in the composition comprising HCFO-1233zdE.

The alkene compounds according to the invention are propene, butenes, pentenes and hexenes. Butenes and pentenes are preferred. Pentenes are even more particularly preferred.

The alkene compounds according to the invention may have a linear or branched chain, preferably a branched chain.

Preferably, they have a boiling point of less than or equal to 100° C., more preferably less than or equal to 75° C., more particularly preferably less than or equal to 50° C.

The term "boiling point" means the boiling point at a pressure of 101.325 kPa, such as determined according to the standard NF EN 378-1 of April 2008.

Preferably also, they have a solidification temperature of less than or equal to 0° C., preferably less than or equal to −25° C., and more particularly preferably less than or equal to −50° C.

The solidification temperature is determined according to Test No. 102: Melting point/Melting range (OECD guidelines for the testing of chemical products, Section 1, OECD Editions, Paris, 1995, available at the address http://dx.doi.org/10.1787/9789264069534-fr).

Alkene compounds according to the invention are notably:
but-1-ene;
cis-but-2-ene;
trans-but-2-ene;
2-methylprop-1-ene;
pent-1-ene;
cis-pent-2-ene;
trans-pent-2-ene;
2-methylbut-1-ene;
2-methylbut-2-ene; and
3-methylbut-1-ene.

Among the preferred compounds, mention may notably be made of 2-methylbut-2-ene, of formula (CH3)2C=CH—CH3 (boiling point of about 39° C.).

Two or more than two of the above compounds may also be used in combination.

The alkene compounds according to the invention are thus advantageously used in combination with HCFO-1233zd, and more particularly they are mixed with HCFO-1233zdE, to provide heat transfer fluids used in heat transfer applications.

The mass proportion of the above alkene compounds in the heat transfer fluid may notably be: from 0.01% to 0.05%; or from 0.05% to 0.1%; or from 0.1% to 0.2%, or from 0.2% to 0.3%; or from 0.3% to 0.4%; or from 0.4% to 0.5%; or from 0.5% to 0.6%; or from 0.6% to 0.7%; or from 0.7% to 0.8%; or from 0.8% to 0.9%; or from 0.9% to 1%; or from 1% to 1.2%; or from 1.2% to 1.5%, or from 1.5% to 2%; or from 2% to 3%; or from 3% to 4%; or from 4% to 5%.

The heat transfer fluid may comprise HCFO-1233zdE and optionally HCFO-1233zdZ. Advantageously, the proportion of HCFO-1233zdE, relative to the total amount of HCFO-1233zd, is of greater than or equal to 90%, or to 91%, or to 92%, or to 93%, or to 94%, or to 95%, or to 96%, or to 97%, or to 98%, or to 99%, or to 99.1%, or to 99.2%, or to 99.3%, or to 99.4%, or to 99.5%, or to 99.6%, or to 99.7%, or to 99.8%, or to 99.9%, or to 99.91%, or to 99.92%, or to 99.93%, or to 99.94%, or to 99.95%, or to 99.96%, or to 99.97%, or to 99.98%, or to 99.99%.

The presence of the alkene compound makes it possible to limit or to prevent an increase in the proportion of HCFO-1233zdZ in the composition over time and/or in the case of the application of relatively high temperatures. The presence of the alkene compound also makes it possible to limit the concentration of the fluoride and chloride ions present in the composition and more generally to limit the degradation of HCFO-1233zdE.

Moreover, the alkene compound is also capable of having a heat transfer function, just like HCFO-1233zdE and the other optional heat transfer compounds. In certain embodiments, it is capable of forming azeotropic or quasi-azeotropic mixtures with HCFO-1233zdE (and, where applicable, with other heat transfer compounds that may be present).

The heat transfer fluid may optionally be combined with various additives, to form therewith a heat transfer composition. The additives may notably be chosen from lubricants, nanoparticles, stabilizers (different from the stabilizer compounds of the invention), surfactants, tracing agents, fluorescent agents, odorants and solubilizers.

The stabilizer(s), when they are present, preferably represent not more than 5% by mass in the heat transfer composition. Among the stabilizers, mention may notably be made of nitromethane, ascorbic acid, terephthalic acid, azoles such as tolutriazole or benzotriazole, phenolic compounds such as tocopherol, hydroquinone, t-butyl hydroquinone, 2,6-di-tert-butyl-4-methylphenol, epoxides (optionally fluorinated or perfluorinated alkyl or alkenyl or aromatic) such as n-butyl glycidyl ether, hexanediol diglycidyl ether, allyl glycidyl ether, butylphenylglycidyl ether, phosphites, phosphonates, thiols, limonene, limonene oxide and lactones.

As lubricants, use may notably be made of oils of mineral origin, silicone oils, paraffins of natural origin, naphthenes, synthetic paraffins, alkylbenzenes, poly-alpha-olefins, polyalkene glycols, polyol esters and/or polyvinyl ethers.

However, in certain advantageous embodiments of the invention, the composition of the invention is free of lubricant.

As nanoparticles, use may notably be made of carbon nanoparticles, metal oxides (copper, aluminum), $TiO_2$, $Al_2O_3$, $MoS_2$, etc.

As tracing agents (which can be detected), mention may be made of deuterated or nondeuterated hydrofluorocarbons, deuterated hydrocarbons, perfluorocarbons, fluoroethers, bromine compounds, iodine compounds, alcohols, aldehydes, ketones, nitrous oxide and combinations thereof. The tracing agent is different from the heat transfer compound(s) making up the heat transfer fluid.

As solubilizers, mention may be made of hydrocarbons, dimethyl ether, polyoxyalkylene ethers, amides, ketones, nitriles, chlorocarbons, esters, lactones, aryl ethers, fluoroethers and 1,1,1-trifluoroalkanes. The solubilizer is different from the heat transfer compound(s) making up the heat transfer fluid.

As fluorescent agents, mention may be made of naphthalimides, perylenes, coumarins, anthracenes, phenanthracenes, xanthenes, thioxanthenes, naphthoxanthenes, fluoresceins and derivatives and combinations thereof.

As odorant agents, mention may be made of alkyl acrylates, allyl acrylates, acrylic acids, acryl esters, alkyl ethers, alkyl esters, alkynes, aldehydes, thiols, thioethers, disulfides, allylisothiocyanates, alkanoic acids, amines, norbornenes, norbornene derivatives, cyclohexene, heterocyclic aromatic compounds, ascaridole, o-methoxy(methyl)phenol and combinations thereof.

The heat transfer fluid (and also the heat transfer composition containing same) may also comprise at least one other heat transfer compound, in addition to HCFO-1233zd. Such an optional other heat transfer compound may notably be a hydrocarbon compound, an ether, a hydrofluoroether, a hydrofluorocarbon, a hydrochlorofluorocarbon, a hydrofluoroolefin, a hydrochloroolefin or a hydrochlorofluoroolefin.

By way of example, said other heat transfer compound may be chosen from 1,1,1,4,4,4-hexafluorobut-2-ene (HFO-1336mzz, E or Z isomer), 3,3,4,4,4-pentafluorobut-1-ene (HFO-1345fz), 2,4,4,4-tetrafluorobut-1-ene (HFO-1354mfy), 1,1,1,3,3-pentafluoropropane (HFC-245fa), 2,3,3,3-tetrafluoropropene (HFO-1234yf), 1,3,3,3-tetrafluoropropene (HFO-1234ze), difluoromethane (HFC-32), 1,1,1,2-tetrafluoroethane (HFC-134a), 1,1,2,2-tetrafluoroethane (HFC-134), 1,1-difluoroethane (HFC-152a), pentafluoroethane (HFC-125), 1,1,1,3,3-pentafluorobutane (HFC-365mfc), methoxynonafluorobutane (HFE7100), butane (HC-600), 2-methylbutane (HC-601a), pentane (HC-601), ethyl ether, methyl acetate and combinations thereof.

In the heat transfer fluid, HCFO-1233zd may notably represent, by mass, from 50% to 55% of the fluid; or from 55% to 60% of the fluid; or from 60% to 65% of the fluid; or from 65% to 70% of the fluid; or from 70% to 75% of the fluid; or from 75% to 80% of the fluid; or from 8%0 to 85% of the fluid; or from 85% to 90% of the fluid; or from 90% to 95% of the fluid; or from 95% to 99% of the fluid; or from 99% to 99.5% of the fluid; or from 99.5% to 99.9% of the fluid; or more than 99.9% of the fluid. The HFO-1233zd content may also vary within several of the above intervals: for example, from 50% to 55% and from 55% to 60%, i.e. from 50% to 60%, etc.

The heat transfer composition/heat transfer fluid described above is placed in contact, according to the invention, with at least one molecular sieve which is preferably placed in a cartridge.

The molecular sieve is preferably a zeolitic adsorbent.

The zeolitic adsorbents, or more simply zeolites, that may be used in the context of the present invention, may be of any type known to those skilled in the art, and notably A-type zeolites, faujasite type zeolites, i.e. X-type and LSX (for "Low silica X") zeolites, and Y-type zeolites. It is understood that these various zeolites may be used alone or as a mixture of two or more thereof.

Zeolites are typically crystalline and porous aluminosilicate-based compounds, which have a three-dimensional crystalline structure consisting of an assembly of $SiO_4$ and $AlO_4$ tetrahedra linked together by sharing one or more oxygen atoms. These compounds thus form crystalline networks containing pores of nanometric size.

These structures generally contain cations to make the system electrically neutral, these cations usually being cations comprising sodium, potassium or calcium, but also barium, rare-earth metals or mixtures of two or more of these cations in any proportion.

Generally, the zeolites used are synthetic zeolites obtained in powder form from a process of nucleation and crystallization of aluminosilicate gels. Zeolites of natural origin, for instance zeolites of clinoptilolite, mordenite or chabazite type, which are in general mainly employed for purification or dehydration procedures, may also be used.

According to a preferred embodiment of the present invention, the zeolite(s) used comprise(s) A-type zeolites, faujasite type zeolites, i.e. X-type zeolites, LSX zeolites, and Y-type zeolites.

Zeolites have the following general formula:

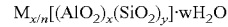

in which:

M represents one or more cations with a total valency n, w represents the number of water molecules, the ratio (y/x) is between 1 and 5 according to the zeolite structures and the sum (x+y) represents the number of tetrahedra per unit cell.

The structure and properties of A-type zeolites are known and widely described in the literature, notably in the book by Donald W. Breck, "Zeolite Molecular Sieves", John Wiley & Sons Eds, (1974), from page 83 onwards, and in U.S. Pat. No. 2,882,243 and FR 1 257 034.

The Si/Al ratio in A-type zeolites is always close to 1. The presence of sodium cations ensures the electrical neutrality of the structure.

Modification of the nature of the cations by total or partial exchange may be accompanied by a variation in the pore size or a modification of the selectivity via the creation of specific interactions with adsorbed molecules, thus altering the adsorption properties.

Thus, for A-type zeolite which, in sodium form after synthesis, has a pore aperture of 4A, various cationic exchanges A may be performed so that it can be given the desired properties.

Frequently, this involves alkali metal or alkaline-earth metal cations such as lithium ($Li^+$), potassium ($K^+$), cesium ($Cs^+$), magnesium ($Mg^{2+}$), calcium ($Ca^{2+}$), strontium ($Sr^{2+}$), barium ($Ba^{2+}$), cerium ($Ce^{3+}$), or others such as rare-earth metals or metals, for example lanthanum ($La^{2+}/La^{3+}$), silver ($Ag^+$), copper ($Cu^{2+}$), nickel ($Ni^{2+}$), zinc, iron, chromium, etc.

Thus, according to the type of cationic exchange performed, A-type zeolite may, for example, be transformed into:
the calcium form via exchange with a calcium salt in aqueous solution, in order to obtain a zeolite having pores with an effective aperture of 5A;
the potassium form via exchange with a potassium salt in aqueous solution in order to obtain a zeolite having pores with an effective aperture of 3A;
various forms, by mixing aqueous solutions of lithium, calcium or potassium salts, for example.

The term "zeolite 4A" means herein an A-type zeolite of which essentially all the exchangeable cationic sites are occupied by sodium cations $Na^+$ (sodium form after synthesis).

The term "zeolite 5A" means herein an A-type zeolite of which at least 40% of the cationic sites (as equivalents) are occupied by $Ca^{2+}$ cations, the remaining sites possibly being occupied by sodium cations $Na^+$; however, it would not constitute a departure from the context of the invention if other cations were present as described previously.

The term "zeolite 3A" means herein an A-type zeolite of which from 20% to 70% (as equivalents) of the exchangeable cationic sites are occupied by potassium cations; however, it would not constitute a departure from the context of the invention if other cations were present as described previously. Faujasites are a group of mineral species characterized by their crystallographic topographic structure, which are notably described in the book by Donald W. Breck "Zeolite Molecular Sieves", John Wiley & Sons Eds, (1974), from page 92 onwards.

The Lowenstein rule imposes thereon an Si/Al mole ratio greater than or at least equal to 1. The following are usually distinguished:
classical X-type faujasites with an Si/Al ratio>1.15;
LSX (for "Low Silica X") faujasites which are X-type zeolitic species with an Si/Al atomic ratio of less than or equal to 1.15, preferably equal to 1±0.05 (the values lower than unity reflect analytical uncertainties in the measurement of this ratio, and the higher values reflect either the same uncertainty or a tolerable deviation of the product purity); and
Y-type faujasites with an Si/Al ratio>1.5.

The elementary cell of the X-type zeolite is a tetrahedron, the apices of which are occupied by polyhedra of the same type as those present in A-type zeolite, each being connected to four other polyhedra via an octahedral substructure, formed by a double ring containing eight oxygen atoms. The center of each edge is always occupied by an oxygen atom, whereas silicon and aluminum atoms occupy the apices of the polyhedra. A preferred form of X-type zeolite is zeolite 13X which has the following chemical formula:

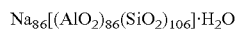

$Na_{86}[(AlO_2)_{86}(SiO_2)_{106}] \cdot H_2O$

X-type and Y-type zeolites are in sodium form after their syntheses: NaX, NaY, LSX zeolite after synthesis is in NaKLSX form.

These zeolites may also undergo exchange or modification treatments and generally it is sought to replace the alkali metal cations (Na, K) for example with protons, alkali metal ions, alkaline-earth metal ions, rare-earth metal or metal ions, for instance those mentioned previously.

The zeolites of the invention may be in the form of a powder or agglomerates. The term "agglomeration" means the shaping of the zeolite powder using a mineral and/or organic binder. This agglomerate shaping may be performed according to any method known to those skilled in the art. For example, the agglomerates may be in the form of platelets, beads with a mean diameter of from a few nanometers to a few millimeters, strands or extrudates, bars, rods, or molded pieces of various sizes and shapes, which may be generically called "cores", etc.

This shaping is performed by mixing a pasty mixture of zeolite(s), binder(s) and optionally one or more additives used, for example, to facilitate the handling of the paste by modifying the rheology and/or the tackiness. This binder, which is usually inert, is used to ensure the cohesion of the crystals of zeolite(s) between them.

Among the mineral binders, use may be made of alumina, montmorillonite (bentonite), attapulgite, sepiolite, zeolitizable clays, such as those chosen from kaolins, kaolinites, nacrites, dickites, halloysites, metakaolins, colloidal clays, for example of the Attagel type or other minerals or zeolites of natural origin (clinoptilolite, mordenite or chabazite), diatomaceous earths, talc, and other mineral binders known to those skilled in the art, which may be used alone or as a mixture of two or more thereof.

Among the organic binders that may be used alone or in combination with the abovementioned mineral binders, any polymer matrix known per se to those skilled in the art of polymers is intended. It may comprise a thermoplastic and/or thermosetting homopolymer and/or copolymer, for example, and in a nonlimiting manner, polyurethane, fluoropolymers such as PVDF, epoxy resins, etc. These polymers may be in any form, for example in the form of an expanded or semi-expanded foam.

As examples of polymer matrices, mention may be made of those described in international patent application WO 2010/063975, in which the polymer matrix comprises a polyolefin (for example of polyethylene, polypropylene etc. type), elastomers (such as those of acrylate copolymer type, for example ethylene/butyl acrylate copolymer), a polyamide, a polyester or a mixture of two or more of these polymers.

The polymer matrix may also comprise, in total or partially, one or more polymers, homo- and/or copolymers, capable of forming a supramolecular assembly. The term "supramolecular assembly" means polymers, homo- and/or copolymers, which can mutually associate through hydrogen bonds.

Among the "supramolecular" polymers, mention may be made, as nonlimiting examples, of semicrystalline polymers, and notably those formed by supramolecular assembly of compounds resulting from the condensation of a fatty acid and/or a fatty acid dimer and/or a fatty acid trimer and at least one associative amine (capable of forming hydrogen bonds) chosen from 1-(2-aminoethyl)imidazolidin-2-one (UDETA), 1-(2-[(2-aminoethyl)amino]ethyl)imidazolidone (UTETA), 1-(2-{2-[(2-aminoethylamino]ethyl}amino)

ethyl]-imidazolidone (UTEPA) and N-(6-aminohexyl)-N-(6-methyl-4-oxo-1,4-dihydropyrimidin-2-yl)urea (UPy), and mixtures thereof.

Besides the mineral and/or organic binders, one or more additives commonly used and known to those skilled in the art may be added to the zeolites, for example additives chosen from silica, colloidal silica, cellulose, corn starch or any other type of pore-forming agent.

Generally, the zeolites used in the present invention may be in any form, for example in the form of a zeolitic agglomerate containing an organic binder, as described in the international patent application WO 2010/063975 for removing water in a double-glazing application, or as described in patents U.S. Pat. Nos. 2,583,812, 4,013,566, and patent applications US 2001/0014707 and EP 1 566 600 in which solids based on zeolites and polymers for drying refrigerant fluids are disclosed.

For the purposes of the invention, the zeolitic agglomerate based on an organic binder is generally obtained from a compound (mixing, then shaping, for example by extrusion, molding, extrusion-molding, injection-extrusion or any other technique known to those skilled in the art for obtaining an article in solid form from at least one molten polymer matrix.

In one embodiment, the adsorbent material according to the present invention may also comprise one or more additives, commonly used in compounding techniques. Nonlimiting examples of such additives may be chosen from UV stabilizers, pigments, colorants, antioxidants, impact modifiers, phase-change materials (PCMs), flame retardants, odorant agents, cellulose, etc., alone or as a mixture.

The zeolitic compounds, whether they are in agglomerated form or in powder form (i.e. non-agglomerated form), which may be used in the context of the present invention may optionally be subjected to an impregnation treatment, for example aqueous phase impregnation using alkali metal and/or alkaline-earth metal hydroxide(s) or via the incorporation of this or these hydroxide(s) and/or carbonate(s) and/or of alkali metal and/or alkaline-earth metal salt(s) before, after or during the agglomeration step and/or before, after or during the shaping step.

The purpose of this impregnation operation is to impregnate the zeolites or zeolitic agglomerates with one or more metals, nonmetals and/or rare-earth metals chosen, for example, from aluminum, scandium, gallium, iron(III), chromium(III), indium, yttrium, lanthanides or more generally rare-earth metals, alone or as a mixture and/or divalent ions chosen from calcium, strontium, zinc, copper, chromium(II), iron(II), manganese, nickel or cobalt ions, alone or as a mixture.

According to another aspect, it should be understood that treatments aimed at effecting the cationic exchanges or modifications defined above may be performed either on zeolite crystals (powder) or on already shaped zeolites (agglomerated, impregnated, etc.), or before and after shaping the zeolitic adsorbents.

According to a preferred embodiment of the present invention, the zeolitic adsorbents are based on A-type zeolite or on faujasite type zeolite, and even more preferably, the zeolitic adsorbents are based on A-type zeolite(s) (3A, 4A or 5A) and/or on zeolite 13X and more preferably either zeolite 3A powder or agglomerates based on A-type zeolite powder, exchanged with potassium, the potassium exchange possibly being performed on the initial powder and/or on the final agglomerate.

According to certain embodiments, two or more than two zeolitic adsorbents may be used. These embodiments are preferred, given the different properties of zeolites regarding air and water adsorption. More precisely, some zeolites such as zeolite 3A are particularly efficient for adsorbing water, whereas other zeolites such as zeolite 5A or zeolite 13X are particularly efficient for adsorbing air. Thus, using them in combination may afford more efficient protection against air and water. For example, the two or more than two zeolitic adsorbents may be zeolite 13X and zeolite 3A, or zeolite 3A and zeolite 5A, or zeolite 13X, zeolite 3A and zeolite 5A.

According to certain preferred embodiments, the two or more than two zeolitic adsorbents may be placed as layers in a cartridge. For example, zeolite 3A may form a first layer, followed by a second layer comprising zeolite 5A and/or zeolite 13X. The term "first layer" means the layer which is the first to be in contact with the stream of heat transfer fluid in the fluid direction.

According to another preferred embodiment, the zeolitic adsorbents that may be used in the context of the present invention are based on A-type zeolites exchanged with potassium, the degree of exchange of which is between 20% and 70% (as molar equivalents) of the total amount of exchangeable cationic sites, preferably between 30% and 70%, more preferably between 40% and 70% and most particularly preferably between 50% and 70%.

When the zeolitic adsorbents are zeolite agglomerates, the agglomeration binder is preferably attapulgite, colloidal attapulgite, sepiolite, bentonite, kaolin, halloysite, these agglomeration binders possibly being used alone or as mixture(s) with other clays or zeolites of natural origin (clinoptilolite, mordenite or chabazite). Preferably, the agglomeration binder mainly contains attapulgite or kaolin and even more preferably attapulgite.

As nonlimiting examples of zeolitic adsorbents that may be used in the context of the present invention, mention may be made of the adsorbents sold by CECA under the names Siliporite® H3Ri, Siliporite® NK10, Siliporite® NK30, Siliporite® SA 1720, Siliporite® NK20, Siliporite® G5 XP, those sold by ZEOCHEM under the names Purmol® 3ST (3A), Purmol® 4ST (A), Zeochem® Z4-01, Zeochem® 4A-8BL, or those sold by GRACE under the names Sylosiv®, Cryosiv®, or by UOP under the names Molsiv™ 3A, Molsiv™ 4A, Molsiv™ 5A, XH-7™, XH-9™ and XH-11™.

According to certain embodiments, one or more compounds that are capable of removing the traces of acidity present in the heat transfer fluid may also be used in combination with the molecular sieves, and notably with the zeolitic adsorbents. This or these compounds may be chosen from metal oxides such as aluminum oxide, alkaline-earth metal oxides, alkali metal oxides, metal hydroxides such as aluminum hydroxide, alkaline-earth metal hydroxides, alkali metal hydroxides, aluminosilicate minerals such as andalusite, disthene, sillimanite, calcium aluminosilicate, sodium aluminosilicate and silicon oxide. Preferably, this compound is aluminum oxide and more preferably this compound is activated aluminum oxide. Activated aluminum oxide is a granular and porous substance which may be manufactured from aluminum hydroxide via its dehydroxylation to produce a highly porous material. Activated alumina may have a surface area of greater than 200 $m^2/g$.

Molecular sieves such as zeolitic adsorbents adsorb air and water, which makes it possible to reduce the reactivity of the medium and thus reduce the acidity. However, it is preferred to also use one or more compounds mentioned above, for the removal of any trace of acidity.

In the case where one or more compounds capable of removing traces of acidity are used, this or these compounds may also be in the form of at least one layer in the cartridge comprising the zeolitic adsorbent(s). The layer comprising the compound(s) capable of removing the traces of acidity is preferably placed upstream of the layer(s) comprising the molecular sieves (notably zeolitic adsorbents) and in particular upstream of the first layer comprising the zeolitic adsorbent (relative to the direction of circulation of the stream of heat transfer fluid).

Alternatively, this or these compounds may be used as a mixture with the molecular sieve(s).

The invention is preferably implemented in a heat transfer facility comprising a vapor compression system.

The heat transfer facility is used for a heat transfer process. The heat transfer process may be a process for heating or cooling a fluid or a body.

The heat transfer facility may also be used in a process for producing mechanical work or electricity, notably in accordance with a Rankine cycle.

For heating and cooling applications, the vapor compression system comprises at least one evaporator, one compressor, one condenser and one pressure regulator, as well as lines for transporting the heat transfer fluid between these elements. The evaporator and the condenser comprise a heat exchanger for exchanging heat between the heat transfer fluid and another fluid or body.

Use may notably be made, as compressor, of a single-stage or multistage centrifugal compressor or of a mini centrifugal compressor. Rotary, scroll, reciprocating or screw compressors may also be used. The compressor may be driven by an electric motor or by a gas turbine (for example fed by the exhaust gases of a vehicle, in the case of mobile applications) or a set of gears.

The vapor compression system then runs according to a standard vapor compression cycle. The cycle comprises the change of state of the heat transfer fluid from a liquid phase (or liquid/vapor dual phase) to a vapor phase at a relatively low pressure, then the compression of the fluid in the vapor phase up to a relatively high pressure, the change of state (condensation) of the heat transfer fluid from the vapor phase to the liquid phase at a relatively high pressure, and the reduction of the pressure to recommence the cycle.

Preferably, the molecular sieve is arranged in a cartridge as described above, which is placed in the vapor compression system or in a system of organic Rankine cycle type. The fluid passing through the cartridge may be in vapor form, liquid form or dual phase form (liquid and vapor). The cartridge may be placed upstream or downstream of a pressure regulator, a compressor, a turbine or between a series of exchangers. Preferably, the cartridge may be placed in the zone having the lowest temperature, i.e. between the turbine and the liquid pump in an organic Rankine cycle. Preferably, the fluid passing through the cartridge is in liquid form.

The heat transfer facility may also optionally comprise at least one coolant fluid circuit used for the transfer of heat (with or without a change of state) between the heat transfer fluid circuit and the fluid or body to be heated or cooled.

The heat transfer facility may also optionally comprise two (or more) vapor compression systems, containing heat transfer fluids which may be identical or different. For example, the vapor compression systems may be coupled to each other.

The cooling processes and facilities according to the invention comprise processes and facilities for air conditioning (with mobile facilities, for example in vehicles, or stationary facilities), for refrigeration (with mobile facilities, for example in containers, or stationary facilities) and for freezing or cryogenics.

The heating facilities according to the invention comprise heat pumps.

For the applications for producing mechanical work or electricity, the heat transfer facility is a heat engine, which comprises at least one evaporator, an expansion member, a condenser and a pump, as well as lines for transporting the heat transfer fluid between these elements. The heat transfer facility may then be run as a Rankine cycle.

Preferably, the molecular sieve is arranged in a cartridge as described above, which is placed in the thermodynamic system, preferably after the expansion member. Thus, the heat transfer fluid exiting the expansion member passes through the cartridge comprising the molecular sieve.

As expansion members, use may notably be made either of turbines having one or more stages, or of pressure regulators. By way of example, rotary, spiral, reciprocating or screw pressure regulators may also be used.

It is possible to use any type of heat exchanger for implementing the heat transfer fluids according to the invention, and notably cocurrent heat exchangers or, preferably, countercurrent heat exchangers.

In particular, the evaporator used in the context of the invention may be a dry-expansion evaporator or a flooded evaporator. In a dry-expansion evaporator, all of the heat transfer fluid is evaporated at the outlet of the evaporator, and the vapor phase is superheated.

In a flooded evaporator, the heat transfer fluid in liquid form does not totally evaporate. A flooded evaporator includes a separator of liquid phase and of vapor phase.

The invention is particularly useful when such an evaporator is used. Specifically, the stabilizers of the prior art with a high boiling point are inefficient when such an evaporator is employed, as they concentrate in the evaporator and do not migrate with the heat transfer fluid toward the condenser.

The alkene stabilizer compound is not or is virtually not trapped by the molecular sieve. Thus, the combined action of the alkene compound and of the molecular sieve makes it possible to use the heat transfer fluid at high temperatures while limiting the isomerization and the degradation of the fluid.

The invention is thus also particularly useful when a high temperature is present at at least one point in the fluid circuit, and more particularly a temperature of greater than or equal to 100° C., or to 110° C., or to 120° C., or to 130° C., or to 140° C., or to 150° C., or to 160° C., or to 170° C., or to 180° C., or to 190° C., or to 200° C., or to 210° C., or to 220° C., or to 230° C., or to 240° C., or to 250° C., or to 260° C., or to 270° C. Specifically, these are the conditions in which HCFO-1233zdE is most liable to be converted into HCFO-1233zdZ or to be degraded.

In particular, in air conditioning devices, the general operating temperature is lower than 100° C.; however, hot spots at the outlet of the compressor may reach temperatures greater than 100° C., affecting the heat transfer fluid over a small proportion of the total duration of its circulation (for example less than 1%).

In heat pumps, the condensation temperature may reach about 160° C. In this case, the heat transfer fluid may be at a temperature of about 160° C. over a significant proportion of the total duration of its circulation (for example about 50%). Moreover, hot spots between 150 and 200° C. may also be observed at the outlet of the compressor. The impact of a long residence time at temperatures greater than 100° C.

and the existence of spots at temperatures which may be close to, or even greater than, 200° C., thus necessitate a stabilizer.

In engine cycles for electricity production of organic Rankine cycle type, the temperature may reach 165° C. In this case, the heat transfer fluid may be at a temperature of about 165° C. or more over a significant proportion of the total duration of its circulation (for example about 50%). Moreover, hot spots between 180 and 250° C., or greater than 250° C., may also be observed at the inlet of the turbine. The impact of a long residence time at temperatures greater than 100° C. and the existence of spots at temperatures which may be close to, or even greater than, 250° C., thus necessitate a stabilizer.

Also preferably, in the heat transfer facility, the temperature of the composition used as a heat transfer fluid remains greater than the solidification temperature of the alkene compound, in order to avoid any deposition of solid matter in the circuit.

Due to the capacity for operating at higher temperatures, the invention also enables the increase in the superheat of the heat transfer fluid. This increase in the superheat results in an increase in the yield and thus improvement of the system performance.

Thus, the superheat may be of from 1 to 90° C., and preferably from 10 to 80° C. For example, the superheat may be increased from 1 to 5° C.; or from 5 to 10° C.; or from 10 to 15° C.; or from 15 to 20° C.; or from 20 to 25° C.; or from 25 to 30° C.; or from 30 to 35° C.; or from 35 to 40° C.; or from 40 to 45; or from 45 to 50° C.; or from 50 to 55° C.; or from 55 to 60° C.; or from 60 to 65° C.; or from 65 to 70° C.; or from 70 to 75° C.; or from 75 to 80° C.; or from 80 to 85° C.; or from 85 to 90° C.

The term "superheat" (equivalent herein to "evaporator superheat") means the temperature differential between the maximum temperature reached by the heat transfer fluid before the compressor or the turbine (i.e. the maximum temperature reached by the heat transfer fluid at the end of the superheat step which follows the evaporation) and the temperature at the end of the evaporation.

EXAMPLES

The examples that follow illustrate the invention without limiting it.

Example 1

Study of the Thermal Stability of HCFO-1233zdE

An organic Rankine cycle operating between a room temperature of 30° C. and a hot source temperature of between 300 and 600° C. and using HCFO-1233zdE as heat transfer fluid, is considered. The HCFO-1233zdE temperature may reach a temperature greater than 200° C. at the evaporator outlet.

2-Methylbut-2-ene is used as the alkene compound.

The thermal stability results at 220° C. in sealed tubes are presented in the table below:

| Product | Acidity ($F^-$ and $Cl^-$) ppm |
|---|---|
| HCFO-1233zdE + 0.5 mol % 2-methylbut-2-ene + filtration of the water and air on sieves | <150 |
| HCFO-1233zdE + 0.5 mol % 2-methylbut-2-ene + 0.3 mol % air | 800 to 1200 |
| HCFO-1233zdE + 0.5 mol % 2-methylbut-2-ene + 400 ppm water | 300 to 450 |

Thus, the results show that 2-methylbut-2-ene is capable of reducing the acidity by virtue of the action of the sieves on the water and air. Without using sieves, the results show that the presence of water and air alters the stability of this composition at very high temperatures (>200° C.) despite the presence of 2-methylbut-2-ene.

Example 2

Use of a Cartridge Comprising a Zeolitic Adsorbent

A cartridge comprising a 3A molecular sieve as adsorbent is placed under conditions representative of the turbine outlet of an organic Rankine cycle.

A mixture of heat transfer fluid (HCFO-1233zdE) having a total mass of 1400 g was prepared by adding thereto 0.5% by mass of 2-methylbut-2-ene and 250 ppm of water.

The cartridge comprises 200 g of 3A molecular sieve.

The heat transfer fluid which is in the liquid phase passes through the cartridge at a temperature of 80° C. and a pressure of 7 bar.

The heat transfer fluid was collected and analyzed after passing through the molecular sieve cartridge.

It was found that the water content of the heat transfer fluid was reduced to 15 ppm and that all of the alkene compound 2-methylbut-2-ene was recovered in the heat transfer fluid.

Example 3

Performance of the Organic Rankine Cycle

An analysis of the performance of an organic Rankine cycle operating with HCFO-1233zdE, having an evaporation temperature of 150° C. and a condensation temperature of 40° C., was performed in a facility according to the invention.

The results are presented in the following table:

| Superheat (° C.) | $T_{max}$ evaporator (° C.) | $T_{max}$ heat source (° C.) | Volumetric capacity (%) | Yield (%) |
|---|---|---|---|---|
| 0 | 160 | 165 | 100.00 | 100.00 |
| 3 | 163 | 168 | 96.73 | 102.56 |
| 13 | 173 | 178 | 90.61 | 108.92 |
| 23 | 183 | 188 | 87.22 | 113.86 |
| 33 | 193 | 198 | 84.94 | 118.11 |
| 43 | 203 | 208 | 83.26 | 121.93 |
| 53 | 213 | 218 | 81.97 | 125.45 |
| 65 | 225 | 230 | 80.75 | 129.38 |
| 66 | 226 | 231 | 80.66 | 129.70 |
| 67 | 227 | 232 | 80.57 | 130.01 |
| 68 | 228 | 232 | 80.48 | 130.32 |

The volumetric capacity and yield results are given as percentages relative to the results obtained with 0° C. of superheat.

The above results show that, despite a decrease in the volumetric capacity, the superheat increase of the heat transfer fluid from 0 to 68° C. (which is made possible by means of the invention) enables a 30% yield increase.

The invention claimed is:

1. A process for limiting or preventing the isomerization of trans-1-chloro-3,3,3-trifluoropropene to cis-1-chloro-3,3,3-trifluoropropene, and/or for limiting or preventing the degradation of trans-1-chloro-3,3,3-trifluoropropene, the process comprising placing trans-1-chloro-3,3,3-trifluoropropene in contact with a combination of a C3 to C6 alkene compound including only one double bond and of at least one molecular sieve.

2. The process as claimed in claim 1, in which the alkene compound is a butene or a pentene.

3. The process as claimed in claim 1, in which the alkene compound has:
   a boiling point of less than or equal to 100° C.; and/or
   a solidification temperature of less than or equal to 0° C.

4. The process as claimed in claim 1, in which the alkene compound is 2-methylbut-2-ene.

5. The process as claimed in claim 1, in which the at least one molecular sieve is at least one zeolitic adsorbent.

6. The process as claimed in claim 5, in which the at least one zeolitic adsorbent is chosen from A-type zeolites, faujasite type zeolites, Y-type zeolites, and mixtures thereof.

7. The process as claimed in claim 5, in which the at least one zeolitic adsorbent is chosen from zeolite 3A, zeolite 5A, zeolite 13X and mixtures thereof.

8. The process as claimed in claim 1, in which at least one molecular sieve for adsorbing air and at least one molecular sieve for adsorbing water are placed in contact with trans-1-chloro-3,3,3-trifluoropropene and are arranged in successive layers in a cartridge.

9. The process as claimed in claim 1, in which the alkene compound has:
   a boiling point of less than or equal to 75° C.; and/or
   a solidification temperature of less than or equal to 25° C.

10. The process as claimed in claim 1, in which the alkene compound has:
   a boiling point of less than or equal to 50° C.; and/or
   a solidification temperature of less than or equal to 50° C.

* * * * *